United States Patent [19]

Holmes

[11] 4,133,963

[45] Jan. 9, 1979

[54] PROCESS FOR THE PRODUCTION OF CARBOXYLIC ACIDS

[75] Inventor: Jerry D. Holmes, Longview, Tex.

[73] Assignee: Eastman Kodak Company, Rochester, N.Y.

[21] Appl. No.: 821,423

[22] Filed: Aug. 3, 1977

Related U.S. Application Data

[63] Continuation-in-part of Ser. No. 633,314, Nov. 19, 1975, abandoned.

[51] Int. Cl.$^2$ .................... C07C 51/12; C07C 67/36
[52] U.S. Cl. ........................ 562/519; 252/429 R; 252/430; 252/431 C; 252/431 P; 560/232
[58] Field of Search ............. 260/532, 488 K, 413, 260/514 M; 560/232

[56] References Cited

U.S. PATENT DOCUMENTS

| | | | |
|---|---|---|---|
| 2,729,651 | 1/1956 | Reppe et al. | 260/532 |
| 2,730,546 | 1/1956 | Reppe et al. | 260/532 |
| 3,769,329 | 10/1973 | Paulik et al. | 260/532 |
| 3,855,307 | 12/1974 | Rony et al. | 260/532 |
| 3,856,856 | 12/1974 | Nozaki | 260/532 |

Primary Examiner—Vivan Garner
Attorney, Agent, or Firm—Edward R. Weber; Daniel B. Reece, III

[57] ABSTRACT

A process for the production of a carboxylic acid by the reaction of a liquid lower alkanol with carbon monoxide at a temperature of from about 150° C. to about 250° C. and a carbon monoxide pressure of from about 2,000 psig to about 10,000 psig in the presence of a soluble liquid phase catalyst prepared from the following ingredients: (1) $MX_n$ wherein M is selected from the group consisting of Co and Ni, X is selected from the group consisting of carboxylate anions of from 2 to 10 carbon atoms, halides, oxides, acetyl acetonate, carbon monoxide, and hydrogen: and n is from 1 to 5; (2) $R_3P$ wherein R is alkyl, aryl, or alkylaryl of from 4 to 10 carbon atoms; and (3) hydrogen iodide or an iodide source such as iodine, alkyl iodides and alkali metal or alkaline earth iodides.

14 Claims, No Drawings

PROCESS FOR THE PRODUCTION OF CARBOXYLIC ACIDS

This is a continuation-in-part of application Ser. No. 633,314 filed Nov. 19, 1975, now abandoned.

This invention relates to the production of carboxylic acids and their esters by the interaction of alcohols with carbon monoxide in the presence of carbonylation catalysts. More particularly, this invention relates to contacting a lower aliphatic saturated alcohol in admixture with carbon monoxide with hydrogen at superatmospheric pressure in the liquid phase in the presence of a novel, soluble, liquid phase carbonylation catalyst.

It is widely known that alcohols, in particular methanol, may be carbonylated to form carboxylic acids and esters thereof containing one more carbon atom than the starting alcohol. In these carbonylations either carbon monoxide or mixtures thereof with hydrogen have been used. The reaction conditions as to temperatures and pressures have been varied to a large extent and a number of catalysts have been proposed. It is generally accepted that the carbonyl forming metals of their compounds are the most active catalysts for such carbonylations. They are far superior to other catalysts both in rate of conversion and yields of the desired materials. Nevertheless, the known carbonylation catalysts of this type have some drawbacks. Some of the best catalysts so far known have been nickel or cobalt compounds in combination with iodine either in elemental form or in the form of compounds. The basic reaction follows the equation ROH + CO yields RCOOH. However, to obtain a reasonable reaction rate a mixture of the desired alcohol and water is used. This reaction proceeds according to the formula: $3ROH + 2CO$ yields $RCOOR + RCOOH + H_2O$. In this reaction the ester is formed as a coproduct and if the acid is the desired product the ester must be recycled or hydrolyzed in another reactor to improve the economics of the process. As the reaction proceeds closer to completion the amount of free alcohol available for esterification is reduced and the ratio of acid to ester greatly increases. To make this process economically attractive conditions are necessary which minimize the ester formation and maximize the acid production. This can be done within limits by increasing the amount of water fed with the alcohol, but this also reduces the effective volume of the given reactor. A higher ratio of acid to ester can also be obtained by holding the reactants in the reactor for a longer period of time, but this also reduces the overall productivity of the reactor. Since the ester is hydrolyzed more rapidly in the presence of acidic catalysts to yield the acid and the starting alcohol which is then available for further reaction, one might expect that the addition of excess hydrogen iodide would give high overall acid production. It has been found, however, that when the ratio of hydrogen iodide to nickel or cobalt carbonyl goes over about 2 to 1 the overall rate of the reaction decreases rapidly.

It is therefore an object of our invention to provide for the carbonylation of an alcohol to an acid having one additional carbon atom in improved yields and conversions and without the drawbacks mentioned above.

A further object of our invention is to minimize the formation of esters when the desired product is the acid.

These and other objects of the invention will become apparent from a consideration of the specification and claims of this application.

The instant invention describes a new soluble liquid phase catalyst composition which permits the use of an increased ratio of hydrogen iodide to metal carbonyl containing catalysts and which yields an improved reaction rate and selectivity to acid as opposed to ester formation. The new catalyst substantially accomplishes this by increasing the production of acid by about 25-30% over that obtained at the same reaction conditions with the optimum 2 to 1 ratio of hydrogen iodide to metal carbonyl catalyst. The new catalyst mixture consists of nickel or cobalt carbonyl (formed in situ from the acetate or a similar salt), hydrogen iodide or an iodide source, and an alkyl or aryl phosphine. A typical composition of the starting materials for the formation of the catalyst is as follows: (1) $MX_n$ wherein M is Co or Ni; X is acetate or other carboxylate anion of from 2 to 10 carbon atoms, halide, oxide, acetyl acetonate, carbon monoxide, or hydrogen; and n is an integer of 1 to 5; (2) HI or an iodide source such as iodine, alkyl iodides, alkali metal iodides and alkaline earth iodides; and (3) $R_3P$ wherein R is alkyl, aryl, or alkylaryl of from 4 to 10 carbons. Phosphines of particular interest include those wherein R is butyl, pentyl, hexyl, heptyl, octyl, phenyl, benzyl, tolyl and higher alkyl substituted phenyls. When X is iodide, the component $MX_n$ will also act as a source of iodide. This will permit a commensurate reduction in the quantity of HI or other iodide source used.

A particularly preferred catalyst mixture is a mixture of cobalt carbonyl, hydrogen iodide, and tri-n-butylphosphine wherein the ratio of cobalt ion to hydrogen iodide to phosphine is about 1 to 4 to 1.3. This catalyst has been found to be particularly effective in a reaction conducted at 200° C. and a carbon monoxide pressure of 5000 psi. Under identical charge of methanol and water and identical reaction conditions this catalyst yielded 234 grams of acetic acid (26% conversion) wherein conventional catalysts with a 2:1 ratio of hydrogen iodide to cobalt carbonyl yielded only 185 grams of acid (20.5% conversion). The overall conversion of methanol to the mixture of methyl acetate and acetic acid was essentially the same in both cases showing that the improved catalyst was much more specific for the formation of the desired acetic acid.

Although the ratio of hydrogen iodide to metal carbonylation catalyst in the preferred catalyst described above was 4:1, this ratio can be varied from about 2:1 to about 10:1. For example, the molar ratio of iodide source to Co or Ni can be from about 3:1 to about 6:1. The ratio of tertiary phosphine to metal carbonylation catalyst can be varied from about 0.5:1 to about 10:1. For example, the molar ratio of tertiary phosphine to Co or Ni can be from about 1:1 to about 4:1. Preferably, this ratio will be higher than 1:1 so as to insure an adequate amount of phosphine for stabilizing the metal carbonyl catalyst complex. The reaction can be carried out at carbon monoxide pressures of from about 2,000 psig to about 10,000 psig. At low pressures the rate is very slow. Equipment cost becomes excessive at the high pressure. A good reaction rate can be obtained at pressures of from about 4,000 psig to about 6,000 psig. Reaction temperatures of 150° C. to 250° C. can be used. For example, temperatures of from about 190° C. to about 230° C. can be used with preferred results being obtained at temperatures of from about 200° C. to 220° C. Pure methanol can be used as a feed but better results are obtained when a mixture of water and methanol is used. Additional water assists in forming a higher ratio of acid to ester by hydrolysis of the ester and also increases the overall reaction rate. Since water occupies reactor volume, however, only that amount needed to insure good acid production is desirable. Good results have been obtained at a methanol to water molar ratio of about 1.2:1 but this range may be varied from 100% methanol to about 0.5:1 methanol to water. The ratio of alkanol, e.g. methanol, to water may be varied from about 0.5:1 to about 10:1.

Phosphines are bases and react readily with halogens or acids such as hydroiodic or hydrobromic acid to form fairly stable adducts. Thus, it was quite surprising that addition of phosphine to the usual metal carbonyl-hydrogen iodide catalyst system produces a stabilized metal carbonyl catalyst. Presumably the catalyst stabilization is due to the phosphine complexing with the metal carbonyl. One would normally expect the excess hydrogen iodide to simply react with the phosphine and render it inactive. In general, phosphines complexed with cobalt carbonyl greatly decrease the rate of reaction in the hydroformylation of olefins. Thus, it was quite unexpected that the new catalyst would give rates of reaction as fast and possibly even faster than that normally found with the conventional cobalt carbonyl hydrogen iodide catalyst.

As will be appreciated the operation of the process of the instant application wherein the feed alkanol, the product acid and the catalyst are all liquids may be much simplified over heterogeneous phase systems. In the process of the instant invention a portion of the catalyst is withdrawn with the product stream. The product is then removed from the catalyst by a conventional distillation. The remaining catalyst containing stream may be regenerated as necessary and reintroduced into the reactor in the feed stream.

The process of the instant invention is illustrated in greater detail by the following examples. It is understood that these examples are not intended to limit the invention in any way and obvious modifications will occur to those skilled in the art.

EXAMPLE 1

This example illustrates the effectiveness of the new catalyst mixture. To a 2 liter Hastelloy C autoclave are charged 485 grams of methanol and 221 grams of water in which have been dissolved 2.86 grams of cobalt acetate tetrahydrate, 10.4 grams of 57 percent aqueous hydrogen iodide, and 3.0 grams of tri-n-butyl phosphine. This mixture is heated to 200° C. and then pressured to 5000 psi with carbon monoxide. As the pressure falls to 4500 psi, it is brought back to 5000 psi with additional carbon monoxide. After 3.5 hours the heating is discontinued and the reactor is cooled using cooling coils. The reaction mixture is analyzed by titration and gas liquid chromatography. Based on these results the methanol conversion to acetic acid is calculated to be 26 percent and to methyl acetate 37 percent. Yield based on methanol is 91 percent.

EXAMPLE 2

This example illustrates the most effective cobalt-hydrogen iodide catalyst hereto known and shows it to be inferior to the new catalyst system. The following mixture is charged to the 2 liter autoclave and the same procedure as described in Example 1 is followed.

|  | Grams |
| --- | --- |
| MeOH | 485 |
| $H_2O$ | 223 |
| $Co(OOCCH_3)_2 \cdot 4H_2O$ | 2.86 |
| HI (57%) | 5.2 |

After the same reaction time (3.5 hours) the methanol conversion to acetic acid is 20 percent and to methyl acetate 42 percent. Methanol yield is essentially the same as in Example 1.

EXAMPLE 3

This example shows the inferior results obtained from excess hydrogen iodide when no phosphine is added. Following the same procedure as described in Example 1 the following mixture is charged into the autoclave.

|  | Grams |
| --- | --- |
| MeOH | 485 |
| $H_2O$ | 221 |
| $Co(OOCCH_3)_2 \cdot 4H_2O$ | 2.86 |
| HI (57%) | 10.4 |

At the end of the same reaction time (3.5 hours) the reaction mixture is cooled and analyzed. Methanol conversion to acetic acid is 8 percent and to methyl acetate 17 percent. Yield based on methanol is 55 percent.

EXAMPLE 4

This example shows that the catalyst system of the instant application gives results equivalent to or better than the prior art catalyst systems even at the prior art optimum hydrogen iodide to cobalt ratio of 2 to 1. Following the same procedure as described in Example 1 the following mixture is charged to the autoclave.

|  | Grams |
| --- | --- |
| MeOH | 485 |
| $H_2O$ | 223 |
| $Co(OOCCH_3)_2$ | 2.86 |
| HI (57%) | 5.2 |
| $(C_4H_9)_3P$ | 3.0 |

At the end of the 3.5 hour reaction the methanol conversion to acetic acid is 21% and to methyl acetate it is 44 percent.

The invention has been described in detail with particular reference to certain preferred embodiments thereof, but it will be understood that variations and modifications can be effected within the spirit and scope of the invention.

I claim:

1. A process for the production of a carboxylic acid by the reaction of a liquid lower alkanol with carbon monoxide at a temperature of from about 150° C. to about 250° C. and a carbon monoxide pressure of from about 2,000 psig to about 10,000 psig in the presence of a soluble liquid phase catalyst prepared from the following ingredients: (1) $MX_n$ wherein M is selected from the group consisting of Co and Ni, X is selected from the group consisting of carboxylate anions of from 2 to 10 carbon atoms, halides, oxides, acetyl acetonate, carbon monoxide, and hydrogen; and n is from 1 to 5; (2) $R_3P$ wherein R is alkyl, benzyl, phenyl, or alkylphenyl of from 4 to 10 carbon atoms; and (3) an iodide source selected from the group consisting of hydrogen iodide, iodine, alkyl iodides, alkali metal iodides and alkaline earth iodides, wherein the molar ratio of M to iodide source is in the ratio of from about 1:2 to about 1:10, and the molar ratio of M to $R_3P$ is from about 1:0.5 to about 1:10.

2. The process of claim 1 wherein the molar ratio of M to iodide source is in the ratio of from about 1:3 to about 1:6.

3. The process of claim 1 wherein the molar ratio of M to $R_3P$ is from about 1:1 to about 1:4.

4. The process of claim 1 wherein the temperature is from about 190° C. to about 230° C.

5. The process of claim 1 wherein the carbon monoxide pressure is from about 4,000 psig to about 6,000 psig.

6. The process of claim 1 wherein the alkanol is fed as an aqueous solution wherein the ratio of alcohol to water is from about 0.5:1 to about 10:1.

7. The process of claim 1 wherein R is selected from the group consisting of butyl, pentyl, hexyl, heptyl, octyl, phenyl, benzyl, and tolyl.

8. A process for the production of acetic acid by the reaction of liquid methanol with carbon monoxide at a temperature of from about 150° C. to about 250° C. and a carbon monoxide pressure of from about 2,000 psig to about 10,000 psig in the presence of a soluble liquid phase catalyst prepared from the following ingredients: (1) $CoX_n$ wherein X is selected from the group consisting of carboxylate anions of from 2 to 10 carbon atoms, halides, oxides, acetyl acetonate, carbon monoxide, and hydrogen; and n is 1 to 5: (2) $R_3P$ wherein R is alkyl, benzyl, phenyl, or alkylphenyl of from 4 to 10 carbon atoms; and (3) an iodide source selected from the group consisting of hydrogen iodide, iodine, alkyl iodides, alkali metal iodides and alkaline earth iodides, wherein the molar ratio of Co to iodide source is in the ratio of from about 1:2 to about 1:10, and the molar ratio of Co to $R_3P$ is from about 1:0.5 to about 1:10.

9. The process of claim 8 wherein the molar ratio of Co to iodide source is in the ratio of from about 1:3 to about 1:6.

10. The process of claim 8 wherein the molar ratio of Co to $R_3P$ is from about 1:1 to about 1:4.

11. The process of claim 8 wherein the temperature is from about 190° C. to about 230° C.

12. The process of claim 8 wherein the carbon monoxide pressure is from about 4,000 psig to about 6,000 psig.

13. The process of claim 8 wherein the methanol is fed as an aqueous solution wherein the ratio of alcohol to water is from about 0.5:1 to about 10:1.

14. The process of claim 8 wherein R is selected from the group consisting of butyl, pentyl, hexyl, heptyl, octyl, phenyl, benzyl, and tolyl.

* * * * *